United States Patent
Zhang et al.

(10) Patent No.: US 9,622,687 B2
(45) Date of Patent: Apr. 18, 2017

(54) HALF STEP FREQUENCY FEATURE FOR RELIABLE MOTION CLASSIFICATION

(71) Applicant: QUALCOMM Incorporated, San Diego, CA (US)

(72) Inventors: Lei Zhang, New Brunswick, NJ (US); Sichao Yang, Basking Ridge, NJ (US); Shankar Sadasivam, San Diego, CA (US); Sundar Subramanian, Bridgewater, NJ (US); Xinzhou Wu, Hillsborough, NJ (US)

(73) Assignee: QUALCOMM Incorporated, San Diego, CA (US)

( * ) Notice: Subject to any disclaimer, the term of this patent is extended or adjusted under 35 U.S.C. 154(b) by 451 days.

(21) Appl. No.: 14/476,482

(22) Filed: Sep. 3, 2014

(65) Prior Publication Data
US 2015/0066422 A1    Mar. 5, 2015

Related U.S. Application Data

(60) Provisional application No. 61/874,075, filed on Sep. 5, 2013.

(51) Int. Cl.
| G06F 19/00 | (2011.01) |
|---|---|
| A61B 5/11 | (2006.01) |
| G01P 13/00 | (2006.01) |
| G01P 15/00 | (2006.01) |
| G01C 22/00 | (2006.01) |

(52) U.S. Cl.
CPC ........... *A61B 5/1123* (2013.01); *A61B 5/1118* (2013.01); *A61B 5/1126* (2013.01); *G01C 22/006* (2013.01); *G01P 13/00* (2013.01); *G01P 15/00* (2013.01)

(58) Field of Classification Search
CPC ....... G06F 3/011; G06F 3/017; G01C 22/006; G10H 1/34
USPC ................. 702/141, 150, 160, 182–185, 188
See application file for complete search history.

(56) References Cited

U.S. PATENT DOCUMENTS

| 5,908,396 A | 6/1999 | Hayakawa et al. |
|---|---|---|
| 6,095,984 A | 8/2000 | Amano et al. |
| 7,421,369 B2 | 9/2008 | Clarkson |
| 2004/0186695 A1 | 9/2004 | Aoshima et al. |
| 2011/0257489 A1 | 10/2011 | Banet et al. |

(Continued)

FOREIGN PATENT DOCUMENTS

| JP | H112542 A | 1/1999 |
|---|---|---|
| WO | 2011092549 | 8/2011 |
| WO | 2012089278 | 7/2012 |

OTHER PUBLICATIONS

International Search Report and Written Opinion—PCT/US2014/054144—ISA/EPO—Nov. 19, 2014.

*Primary Examiner* — Edward Raymond
(74) *Attorney, Agent, or Firm* — Blakely Sokoloff Taylor & Zafman

(57) ABSTRACT

Disclosed is an apparatus and method for classifying a motion state of a mobile device. In one embodiment, accelerometer data representing acceleration components along orthogonal x, y, and z axes of the mobile device are collected. A presence or absence of a half-step frequency relationship between the accelerometer data is determined. Last, the motion state of the device is determined based at least in part on the presence or absence of the half-step frequency relationship.

32 Claims, 9 Drawing Sheets

(56) References Cited

U.S. PATENT DOCUMENTS

| | | |
|---|---|---|
| 2013/0054181 A1 | 2/2013 | Lakhzouri et al. |
| 2013/0190903 A1 | 7/2013 | Balakrishnan et al. |
| 2015/0316579 A1* | 11/2015 | Pakzad .................. G01P 15/02 |
| | | 702/150 |
| 2016/0019731 A1* | 1/2016 | Hanson ................ G01G 19/024 |
| | | 701/29.1 |

* cited by examiner

Walking

Running

HALF STEP FREQUENCY FEATURE FOR RELIABLE MOTION CLASSIFICATION

CROSS REFERENCE TO RELATED APPLICATIONS

The present application claims priority to U.S. Provisional Patent Application No. 61/874,075, filed Sep. 5, 2013, entitled "Half Step Frequency Feature for Reliable Motion Classification," the content of which is hereby incorporated by reference in its entirety for all purposes.

FIELD

The subject matter disclosed herein relates generally to motion and activity classification using sensors on a mobile device.

BACKGROUND

Classifying physical motion contexts of a mobile device is useful for various applications. Such applications may include motion-aided geo-fencing, motion-aided Wi-Fi scan optimization, distracted pedestrian detection, health monitoring, etc. Common classifications may include walking, running, biking, fiddling, and being stationary, etc.

Motion contexts of a mobile device can be established through gathering and processing data received from sensors embedded in the mobile device. Mobile devices are now coming equipped with tri-axial accelerometers. A tri-axial accelerometer is a low-power sensor that can provide acceleration data representing acceleration components along orthogonal x, y, and z axes. A user's physical motion is transferred to a mobile device and the accelerometer embedded therein by either direct or indirect physical connection, such as by the user holding the mobile device in hand, or by the user keeping the mobile device in a pocket.

SUMMARY

Disclosed is a method of classifying a motion state of a mobile device comprising: collecting accelerometer data representing acceleration components along orthogonal x, y, and z axes of the mobile device; determining a presence or absence of a half-step frequency relationship between the accelerometer data; and determining the motion state of the device based at least in part on the presence or absence of the half-step frequency relationship.

Further disclosed is an apparatus for classifying a motion state of a mobile device comprising: a memory; and a processor configured to: collect accelerometer data representing acceleration components along orthogonal x, y, and z axes of the mobile device, determine a presence or absence of a half-step frequency relationship between the accelerometer data, and determine the motion state of the device based at least in part on the presence or absence of the half-step frequency relationship.

Further disclosed is an apparatus for classifying a motion state of a mobile device comprising: means for collecting accelerometer data representing acceleration components along orthogonal x, y, and z axes of the mobile device; means for determining a presence or absence of a half-step frequency relationship between the accelerometer data; and means for determining the motion state of the device based at least in part on the presence or absence of the half-step frequency relationship.

Further disclosed is a non-transitory computer-readable medium including code which, when executed by a processor, causes the processor to perform a method comprising: collecting accelerometer data representing acceleration components along orthogonal x, y, and z axes of the mobile device; determining a presence or absence of a half-step frequency relationship between the accelerometer data; and determining the motion state of the device based at least in part on the presence or absence of the half-step frequency relationship.

DETAILED DESCRIPTION

The word "exemplary" or "example" is used herein to mean "serving as an example, instance, or illustration." Any aspect or embodiment described herein as "exemplary" or as an "example" in not necessarily to be construed as preferred or advantageous over other aspects or embodiments.

Figure 1:
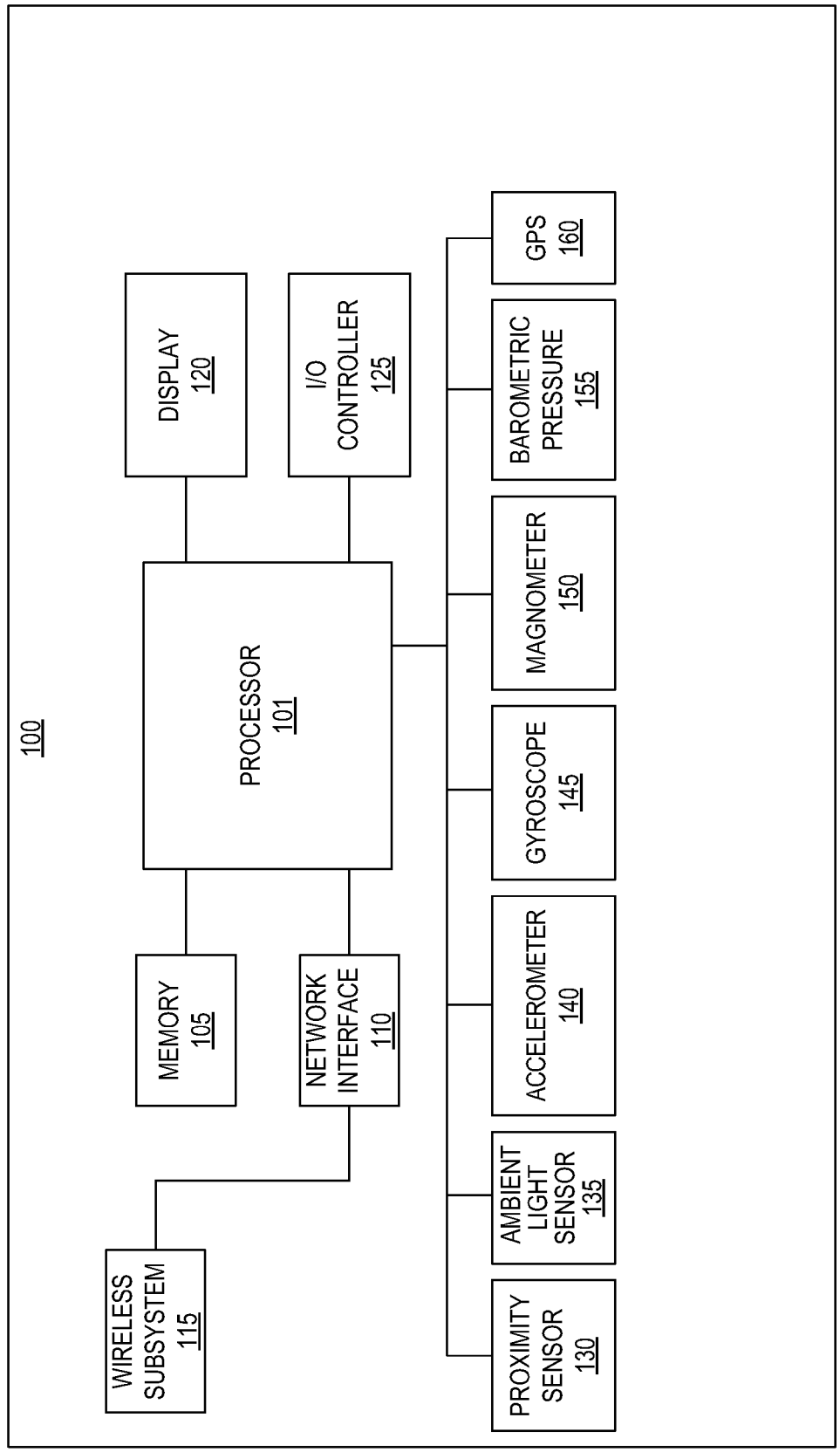
FIG. 1 is a block diagram of a system in which aspects of the invention may be practiced.

FIG. 1 is block diagram illustrating an exemplary device 100 in which embodiments of the invention may be practiced. The device 100 may be a mobile device, which may include one or more processors 101, a memory 105, I/O controller 125, and network interface 110. Thus, the device 100 may be a: mobile device, wireless device, cell phone, personal digital assistant, mobile computer, tablet, head-mounted display (HMD), wearable device, personal computer, laptop computer, or any type of device that has processing capabilities. Device may also include one or more sensors (e.g., a proximity sensor, ambient light sensor (ALS), accelerometer, gyroscope, magnetometer, barometric pressure sensor, Global Positioning System (GPS) sensor) coupled to one or more buses or signal lines further coupled to the processor 101. It should be appreciated that device may also include a display 120, a user interface (e.g., keyboard, touch-screen, or similar devices), a power device (e.g., a battery), as well as other components typically associated with electronic devices. In some embodiments, device 110 may be a mobile device. Network interface 110 may also be coupled to a number of wireless subsystems 115 (e.g., Bluetooth, Wi-Fi, Cellular, or other networks) to transmit and receive data streams through a wireless link to/from a wireless network, or may be a wired interface for direct connection to networks (e.g., the Internet, Ethernet, or other wireless systems).

Device 100 can include sensors such as a proximity sensor 130, ambient light sensor (ALS) 135, accelerometer 140, gyroscope 145, magnetometer 150, barometric pressure sensor 155, and/or Global Positioning Sensor (GPS) 160.

Memory 105 may be coupled to processor 101 to store instructions for execution by processor 101. In some embodiments, memory 105 is non-transitory. Memory 105 may also store one or more models or modules to implement embodiments described below. Memory 105 may also store data from integrated or external sensors.

It should be appreciated that embodiments of the invention as will be hereinafter described may be implemented through the execution of instructions, for example as stored in the memory 105 or other element, by processor 101 of device 100 and/or other circuitry of device and/or other devices. Particularly, circuitry of device, including but not limited to processor 101, may operate under the control of a program, routine, or the execution of instructions to execute methods or processes in accordance with embodiments of the invention. For example, such a program may be implemented in firmware or software (e.g. stored in memory 105 and/or other locations) and may be implemented by processors, such as processor 101, and/or other circuitry of device. Further, it should be appreciated that the terms processor, microprocessor, circuitry, controller, etc., may refer to any type of logic or circuitry capable of executing logic, commands, instructions, software, firmware, functionality and the like.

Further, it should be appreciated that some or all of the functions, engines or modules described herein may be performed by device 100 itself and/or some or all of the functions, engines or modules described herein may be performed by another system or device connected through I/O controller 125 or network interface 110 (wirelessly or wired) to device. Thus, some and/or all of the functions may be performed by another system and the results or intermediate calculations may be transferred back to device. In some embodiments, such other device may comprise a server configured to process information in real time or near real time.

Figure 2:
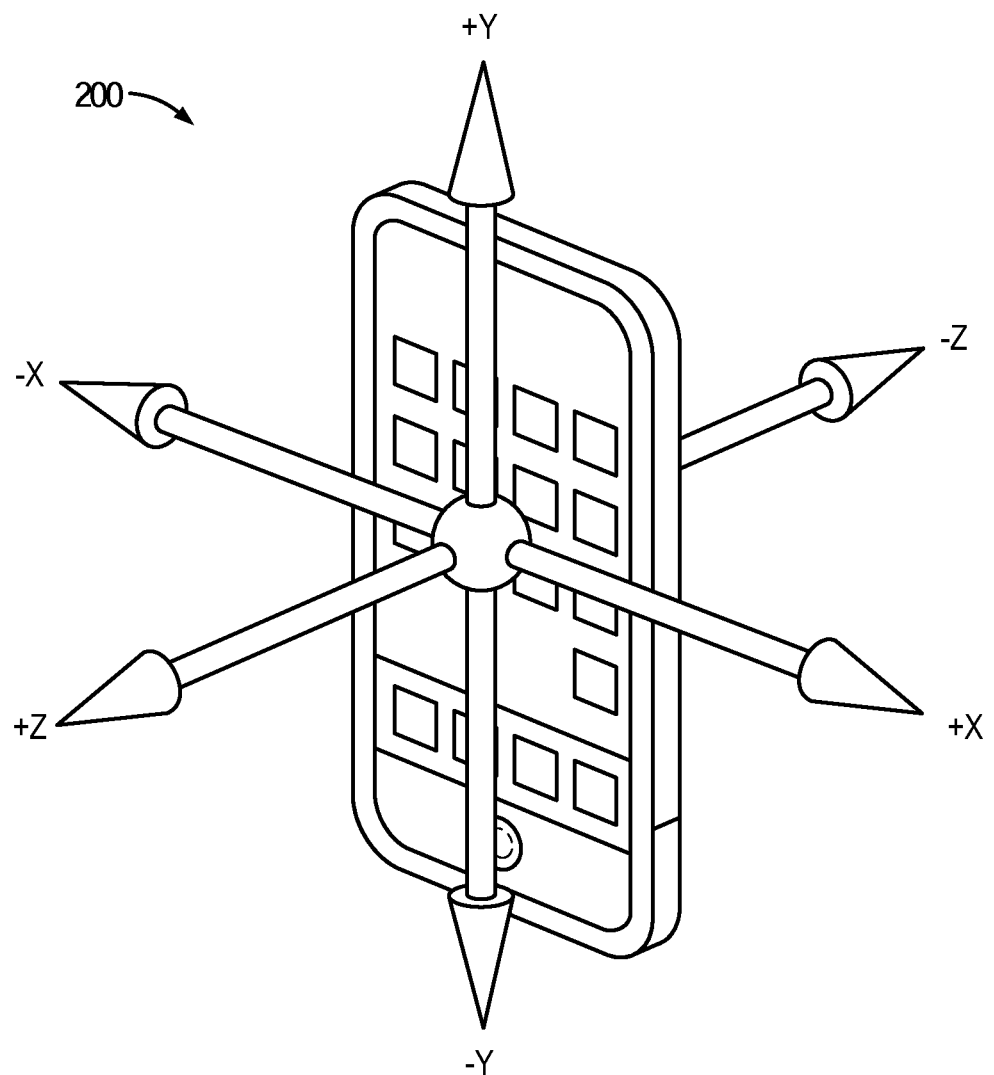
FIG. 2 illustrates a coordinate system of an accelerometer included in a device.

FIG. 2 illustrates an example coordinate system 200 of an example accelerometer 140 included in an example device 100. The x, y, and z axes run along the width, height, and depth of the example device 100, respectively. The accelerometer 140 samples and outputs in real time data representing magnitude and direction of acceleration components along each of the orthogonal x, y, and z axes.

Accelerometer data collected over a period of time is processed and analyzed to determine a motion context classification. Hereinafter the terms "motion context" and "motion state" may be used interchangeably. Conventional methods for classifying motion contexts based on such features of accelerometer data as variance, time correlation, etc., are well known in the art. However, conventional analysis of the features may be insufficient to distinguish certain different motion contexts exhibiting similar characteristics of acceleration in time domain. For example, of particular interest is detecting a user's walking or running activities. Conventional methods for analyzing features of accelerometer data may be insufficient to determine whether the user is walking/running or simply fiddling or shaking the mobile device.

Figure 3A:
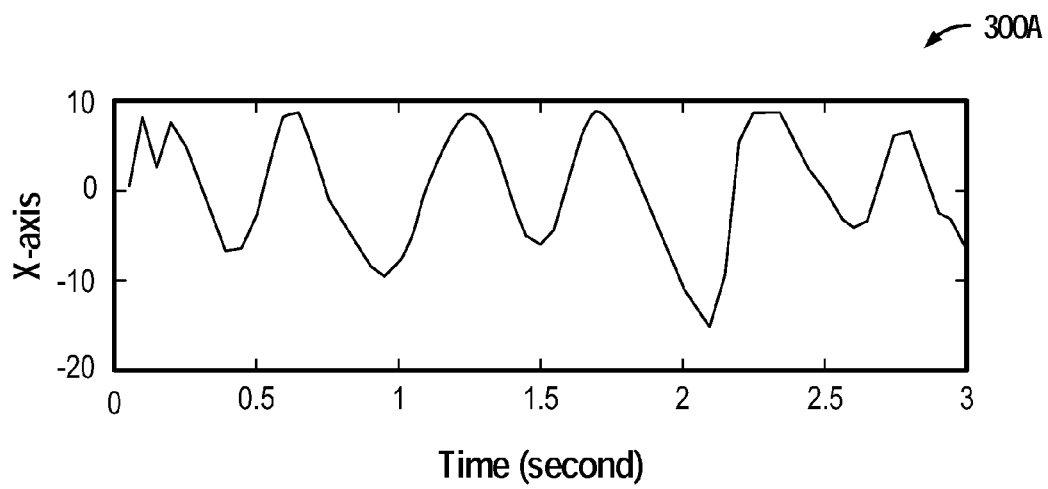
FIG. 3A is a time-domain plot of x-axis accelerometer data obtained in a case where a user is fiddling a device.
Figure 3B:
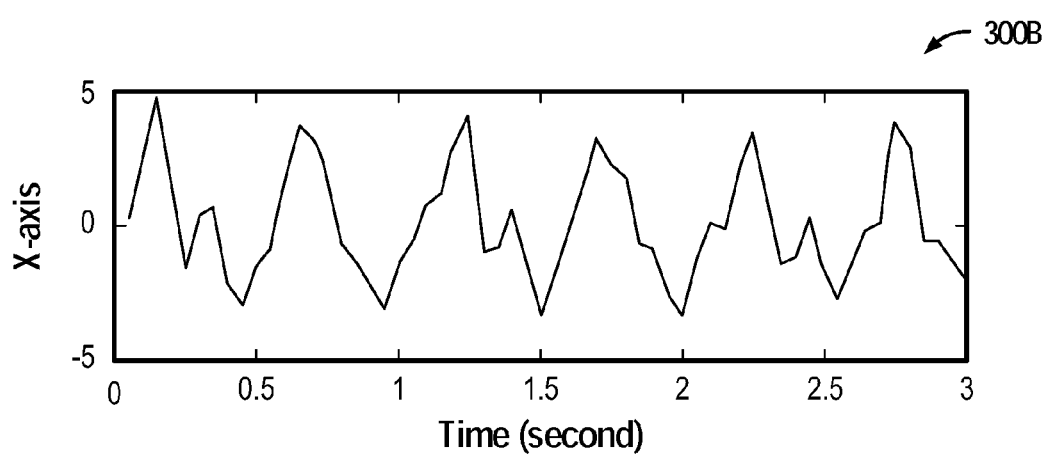
FIG. 3B is a time-domain plot of x-axis accelerometer data obtained in a case where a user is walking.

FIG. 3A is a time-domain plot 300A of example x-axis accelerometer data obtained in a case where a user is fiddling the device 100. FIG. 3B is a time-domain plot 300B of example x-axis accelerometer data obtained in a case where a user is walking. It can be appreciated by a person of ordinary skill in the art that distinguishing data represented in FIG. 3A from data represented in FIG. 3B poses a challenging task.

One embodiment of a method described herein is based on the observation that a motion of a person walking or running has a prominent frequency component on the side-to-side direction which is half the frequency of a prominent frequency component that exists on the up-and-down direction. The half-step frequency relationship may generally be observed and detected within the tri-axial accelerator data while the user is walking/running, although the relationship may manifest itself in different forms, as will be shown below. When the motion of the device is caused by other kinds of user movement, such as shaking, fiddling, or traveling in a vehicle, the half-step frequency relationship is likely to be absent. Various methods for detecting the half-step frequency relationship have been contemplated. For example, in one embodiment, frequency domain analysis may be utilized to detect the half-step frequency relationship. In some other embodiments, time-domain techniques such as the auto-correlation function, peak analysis, machine learning, etc., may be utilized to determine whether the half-step frequency relationship is present.

Figure 4:
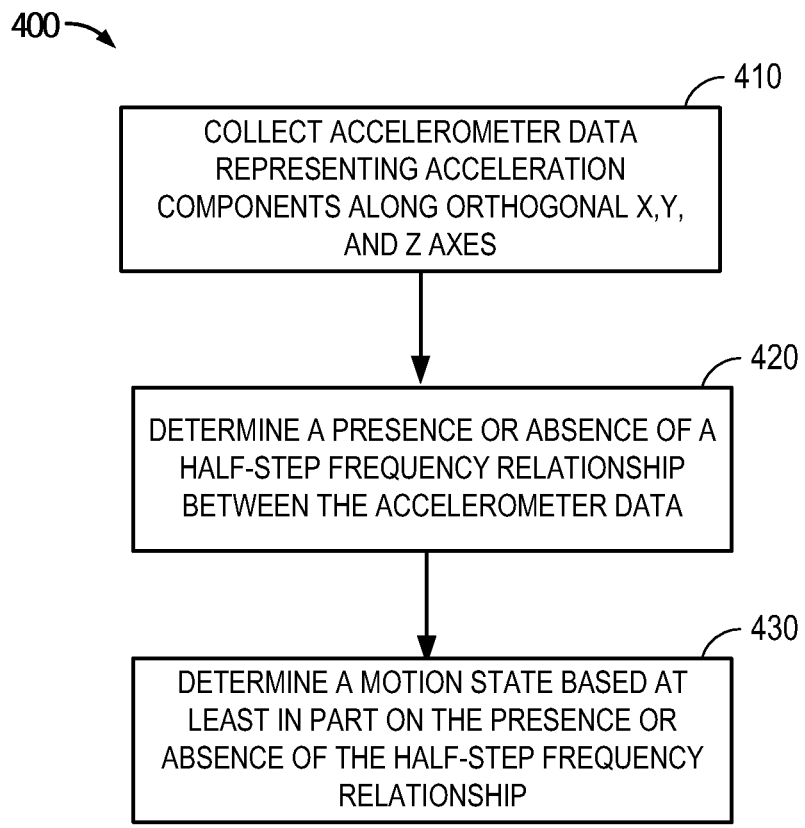
FIG. 4 illustrates a flow diagram of one embodiment of a method of classifying a motion state of a mobile device.

FIG. 4 illustrates a flow diagram of one embodiment of a method 400 of classifying a motion state of a mobile device. At operation 410, accelerometer data representing acceleration components along orthogonal x, y, and z axes of the mobile device are collected. In one embodiment, the collection of accelerometer data is performed over a time window. The duration of the time window may be optimally selected based on the actual implementation. In one embodiment described herein, the duration of the time window is at least three seconds. A shorter time window (e.g., a one-second time window) or a longer time window (e.g., a ten-second time window) may also be utilized. The duration of the time window does not limit the invention. At next operation 420, a presence or absence of a half-step frequency relationship between the data of x, y, and z axes is determined. A half-step frequency relationship is one wherein a peak at one frequency coexists with a peak at half that frequency. The relationship may exist in data within one axis or in data across different axes, depending on the relative location and orientation of the device in relation to the body of the user. Various methods for detecting the half-step frequency relationship have been contemplated. For example, in one embodiment, accelerometer data collected over the time window is transformed from the time domain into a frequency domain, and the determination of whether the half-step frequency relationship is present or absent is made in the frequency domain. Methods for transforming sample data from the time domain into the frequency domain such as the Fast Fourier Transform (FFT), and vice versa, are well known in the art. In some other embodiments, time-domain techniques such as the auto-correlation function, peak analysis, machine learning, etc., may be utilized to determine whether the half-step frequency relationship is present. At next operation 430, a motion state of the mobile device is determined based at least in part on the presence or absence of the half-step frequency relationship. In one embodiment, the determining of the motion state comprises determining a walk/run state based at least in part on the presence of the half-step frequency relationship. The presence of a half-step frequency relationship suggests that the user is walking or running, while the absence of a half-step frequency relationship suggests the user is not walking or running, and the acceleration captured by the accelerometer 140 may be associated with some other type of motion, such as fiddling, traveling in a vehicle, or intentional shaking.

FIGS. 5-8 are frequency-domain plots of example accelerometer data obtained in scenarios where a user is walking or running and performing various other activities at the same time. These figures further illustrate the presence of a half-step frequency relationship in cases where a user is walking/running It should be appreciated that motion context inferences in addition to the determination of whether the user is walking/running may be obtained by analyzing tri-axial accelerator data using known statistical techniques as different motion contexts may be associated with different characteristic patterns in the accelerator data.

Figure 5:
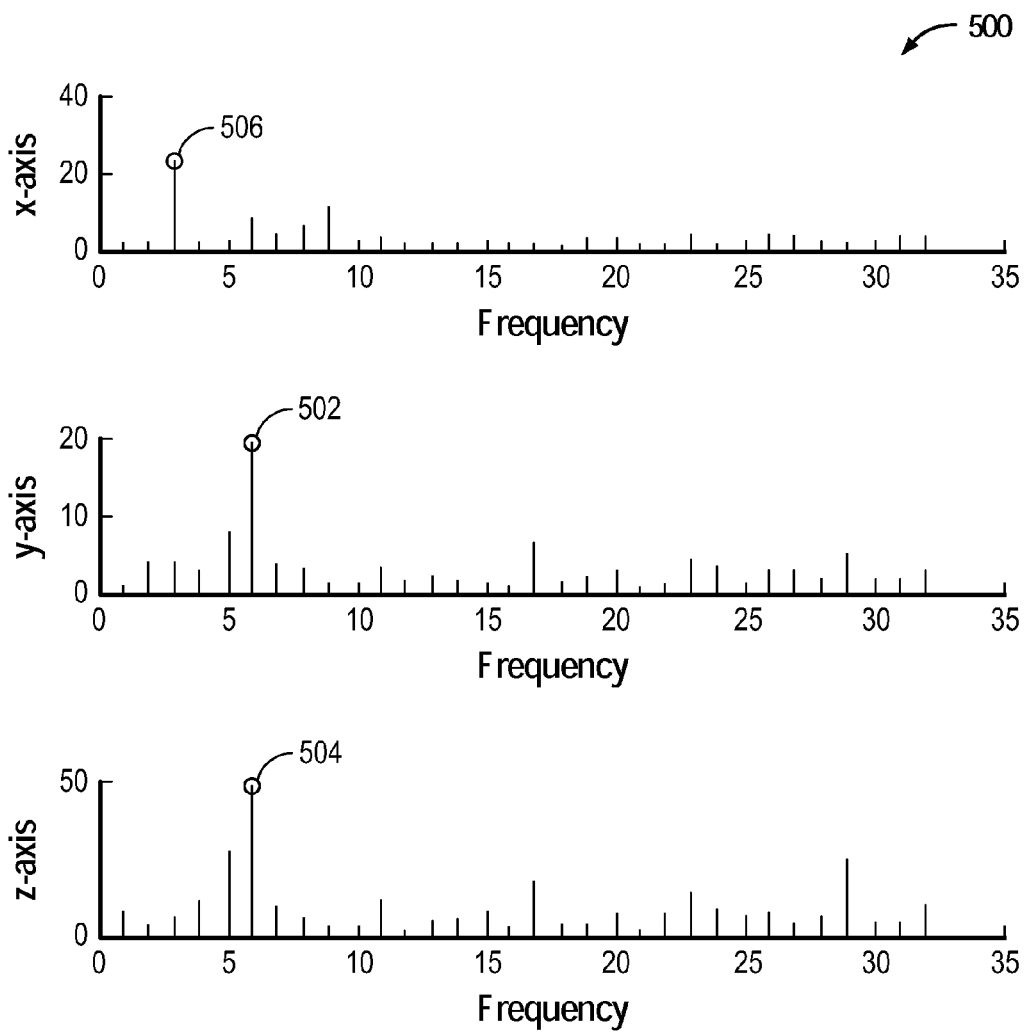
FIG. 5 is a frequency-domain plot of accelerometer data obtained in a case where a user is walking/running and reading from a display of a device at the same time while holding the device in hand.

FIG. 5 is a frequency-domain plot 500 of example accelerometer data obtained in a case where a user is walking/running and reading from an example display 120 of an example device 100 at the same time while holding the device 100 in hand. As can be seen in FIG. 5, a half-step frequency relationship exists for data shown in FIG. 5 because a peak 502, 504 at step frequency f=6 exists on each of y and z axes, while a peak 506 at half-step frequency f/2=3 exists on the x axis. Based upon this type of half-step frequency relationship, the device 100 may determine the user is walking/running and reading at the same time.

Figure 6:
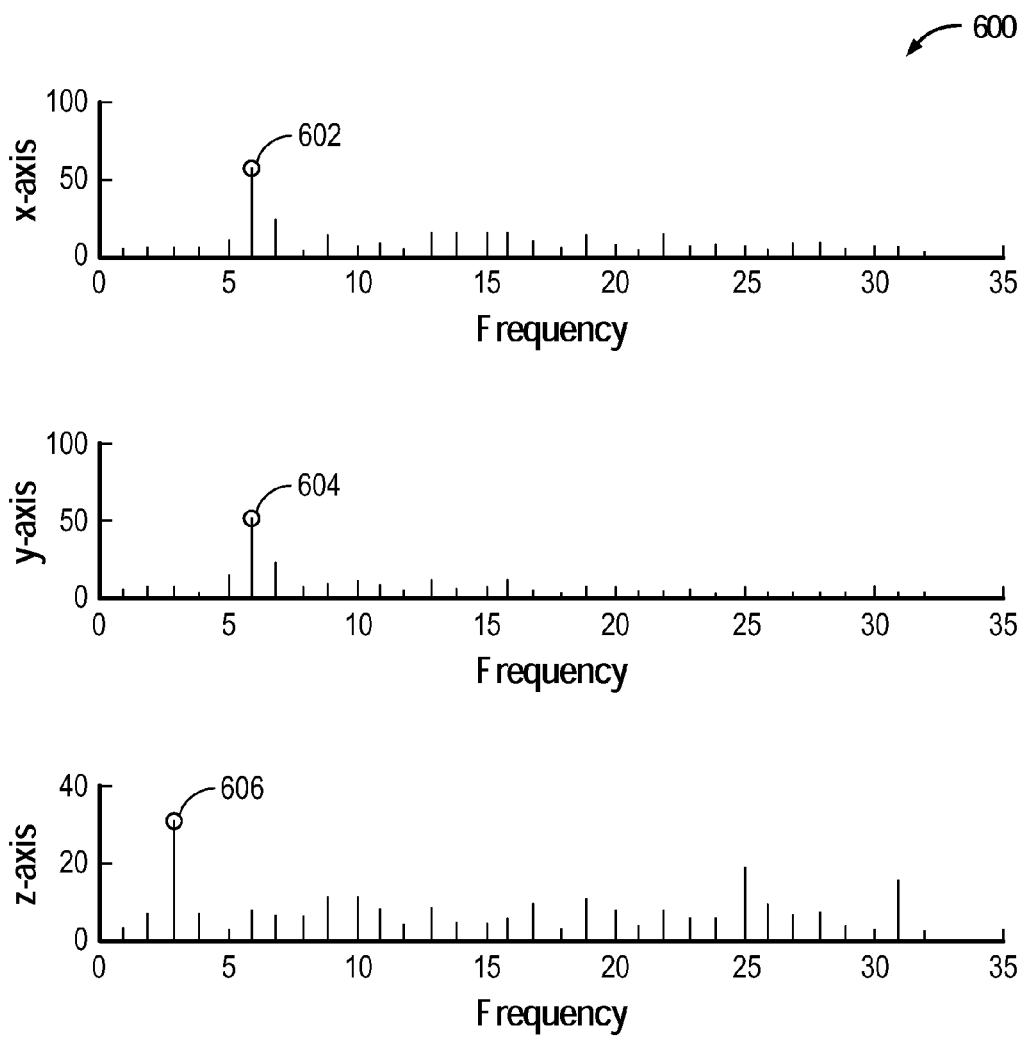
FIG. 6 is a frequency-domain plot of accelerometer data obtained in a case where a user is walking/running and having a phone conversation over a device at the same time while holding the device close to one ear.

FIG. 6 is a frequency-domain plot 600 of example accelerometer data obtained in a case where a user is walking/running and having a phone conversation over an example device 100 at the same time while holding the device 100 close to one ear. As can be seen in FIG. 6, a half-step frequency relationship exists for data shown in FIG. 6 because a peak 602, 604 at step frequency f=6 exists on each of x and y axes, while a peak 606 at half-step frequency f/2=3 exists on z axis. Based upon this type of half-step frequency relationship, the device 100 may determine the user is walking/running and having a phone conversation at the same time.

Figure 7:
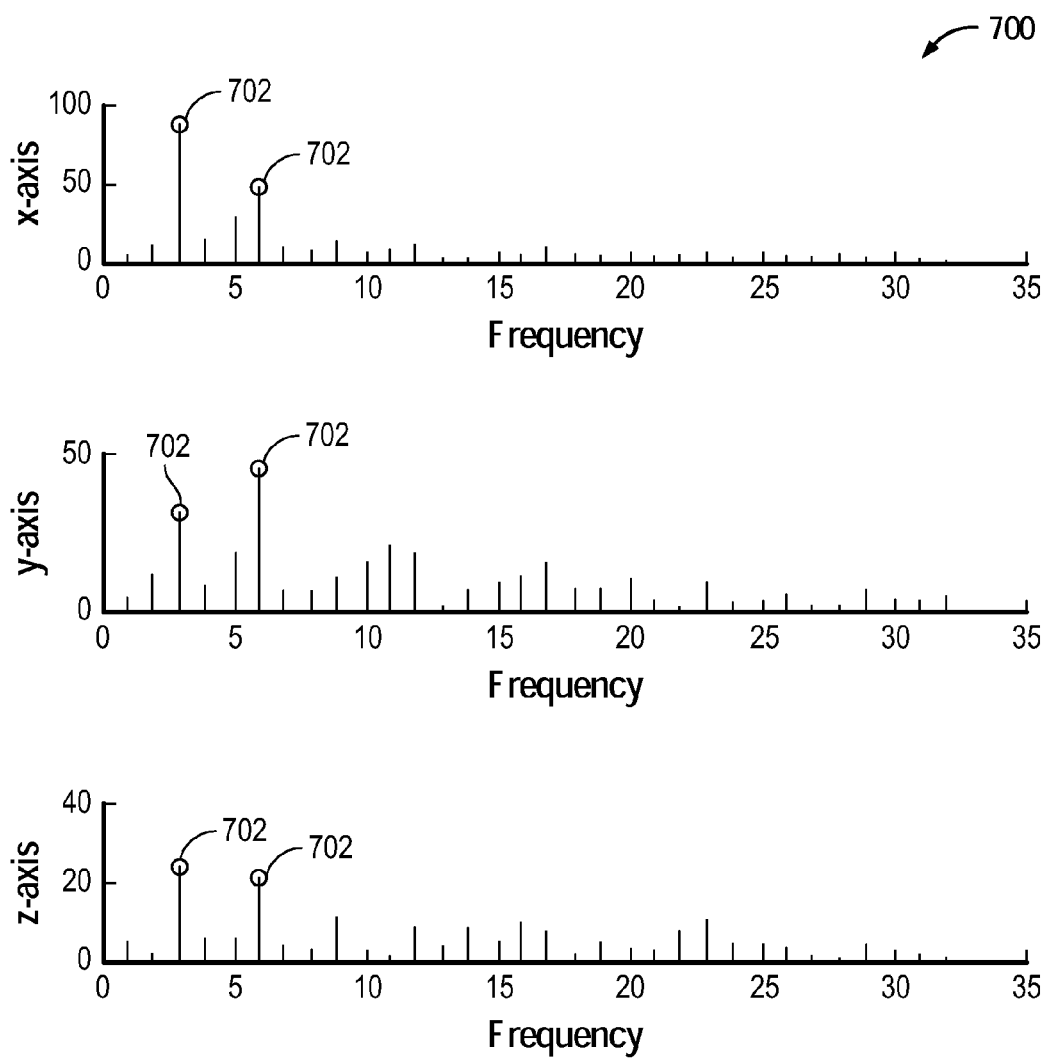
FIG. 7 is a frequency-domain plot of accelerometer data obtained in a case where a user is walking/running and a device is being swung together with the user's swinging arms at the same time.

FIG. 7 is a frequency-domain plot 700 of example accelerometer data obtained in a case where a user is walking/running and an example device 100 is being swung together with the user's swinging arms at the same time. As can be seen in FIG. 7, a half-step frequency relationship exists for data shown in FIG. 7 because a peak 702 at step frequency f=6 and a peak 702 at half-step frequency f/2=3 exist on all x, y, and z axes. Based upon this type of half-step frequency relationship, the device 100 may determine the user is walking/running and swinging arms at the same time.

Figure 8:
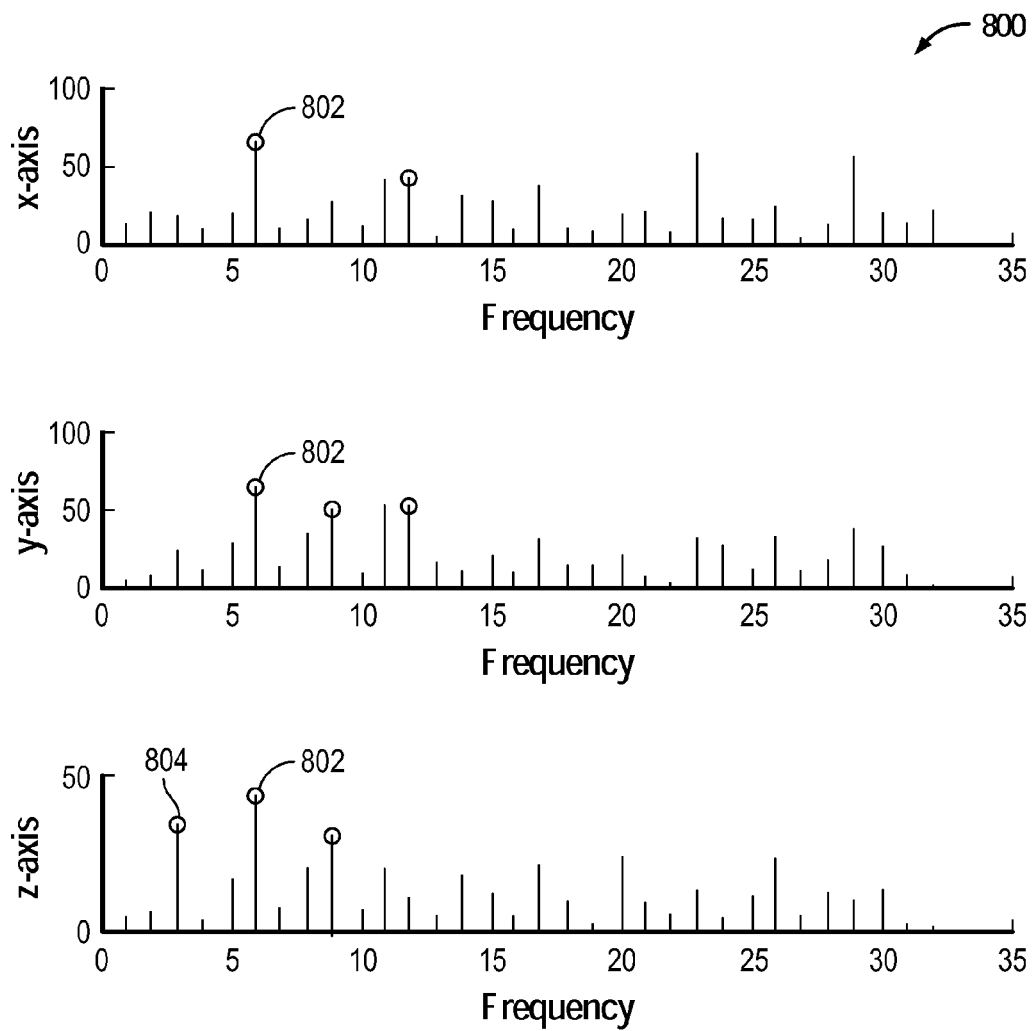
FIG. 8 is a frequency-domain plot of accelerometer data obtained in a case where a user is walking/running and a device is being kept in a pocket or a backpack at the same time.

FIG. 8 is a frequency-domain plot 800 of example accelerometer data obtained in a case where a user is walking/running and an example device 100 is being kept in a pocket or a backpack at the same time. As can be seen in FIG. 8, a half-step frequency relationship exists for data shown in FIG. 8 because a peak 802 at step frequency f=6 exists on all x, y, and z axes, while a peak 804 at half-step frequency f/2=3 exists on z axis. It should also be appreciated that a peak at 3f/2=9 exists on each of y and z axes, and a peak at 2f=12 exists on each of x and y axes. Based upon this type of half-step frequency relationship, the device 100 may determine the user is walking/running and keeping the device 100 in a pocket or in a backpack at the same time.

It should be appreciated from the description of FIGS. 5-8 that the combination of peaks at step frequency f, half-step frequency f/2, frequency 3f/2, and frequency 2f and their existence on each of the axes may be utilized to further classify motion contexts on a more granular level. Such a classification indicates a user is performing an additional activity while walking/running. For example, based on the information disclosed herein, it can be determined probabilistically whether a user is reading, having a phone conversation, swinging arms, or keeping a mobile device in a pocket or in a backpack while walking/running It should also be appreciated that the amplitude of frequency components at step frequency f and half-step frequency f/2 may be utilized to further refine the motion context classification. For example, the amplitude may be used to distinguish walking from running because motion caused by running may be associated with a larger acceleration than motion caused by walking. For example, the amplitude in a case of running can be an order of magnitude larger than in a case of walking. In the time domain, the magnitude of accelerometer readings may be used in a similar fashion. In some embodiments, phase information of the pattern in the accelerometer data may likewise be used to further refine motion state classification.

Figure 9:
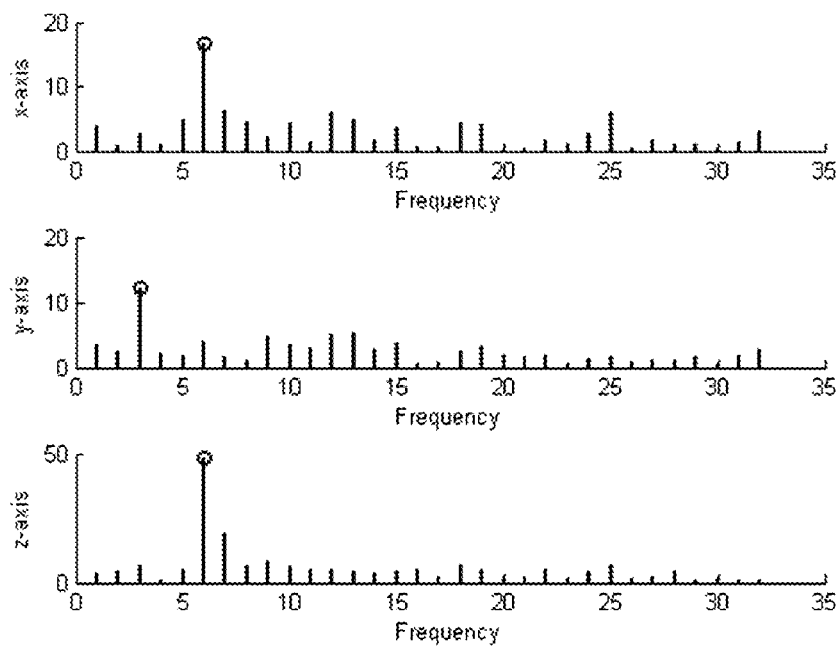
FIG. 9 illustrates frequency-domain plots of exemplary accelerator data obtained when a user is a) walking and b) running
Figure 9:
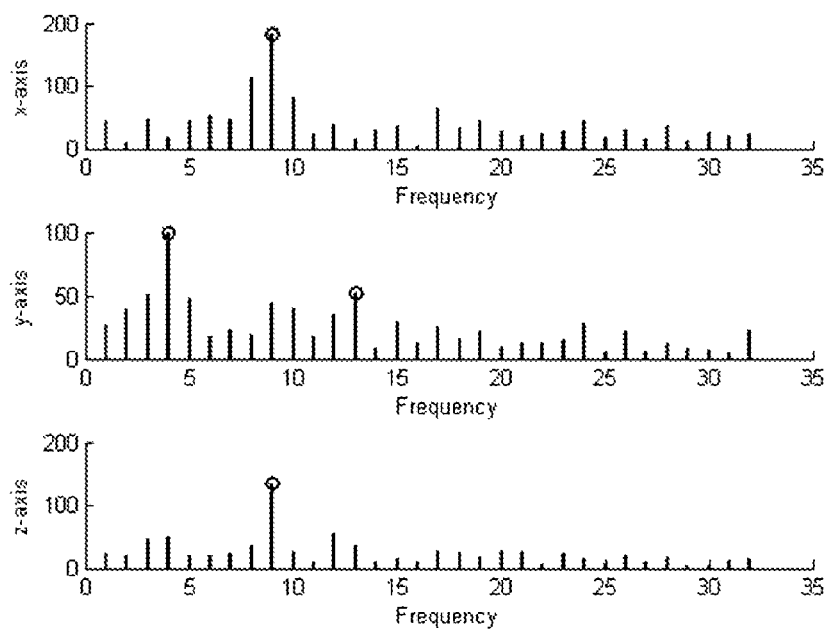

FIG. 9 illustrates frequency-domain plots of exemplary accelerator data obtained when a user is a) walking and b) running It can be seen in FIG. 9 that, in both exemplary cases of walking and running, the half-step frequency component (e.g., f/2) is present only in y-axis data. However, the amplitudes of the frequency peaks are markedly different in the two cases. In particular, the amplitudes of frequency peaks in the case of running is approximately ten times as large as the amplitudes of frequency peaks in the case of walking. Therefore, as described above, the amplitude in the accelerometer data may be utilized to distinguish between motion contexts of walking and running.

By utilizing the method described herein, walking or running activities of a user of a mobile device is more readily ascertainable. A system for motion context classification therefore benefits by being better capable of distinguishing walking/running activities from other types of motion.

It should be appreciated that aspects of the invention previously described may be implemented in conjunction with the execution of instructions (e.g., applications) by processor 101 of device 100, as previously described. Particularly, circuitry of the device, including but not limited to processor, may operate under the control of an application, program, routine, or the execution of instructions to execute methods or processes in accordance with embodiments of the invention (e.g., the processes of FIGS. 4-8). For example, such a program may be implemented in firmware or software (e.g., stored in memory and/or other locations) and may be implemented by processors and/or other circuitry of the devices. Further, it should be appreciated that the terms processor, microprocessor, circuitry, controller, etc., refer to any type of logic or circuitry capable of executing logic, commands, instructions, software, firmware, functionality, etc.

It should be appreciated that when the device is a mobile or wireless device that it may communicate via one or more wireless communication links through a wireless network that are based on or otherwise support any suitable wireless communication technology. For example, in some aspects computing device or server may associate with a network including a wireless network. In some aspects the network may comprise a body area network or a personal area network (e.g., an ultra-wideband network). In some aspects the network may comprise a local area network or a wide area network. A wireless device may support or otherwise use one or more of a variety of wireless communication technologies, protocols, or standards such as, for example, CDMA, TDMA, OFDM, OFDMA, WiMAX, 3G, LTE, LTE Advanced, 4G, and Wi-Fi. Similarly, a wireless device may support or otherwise use one or more of a variety of corresponding modulation or multiplexing schemes. A mobile wireless device may wirelessly communicate with other mobile devices, cell phones, other wired and wireless computers, Internet web-sites, etc.

The teachings herein may be incorporated into (e.g., implemented within or performed by) a variety of apparatuses (e.g., devices). For example, one or more aspects taught herein may be incorporated into a phone (e.g., a cellular phone), a personal data assistant (PDA), a tablet, a mobile computer, a laptop computer, a tablet, an entertainment device (e.g., a music or video device), a headset (e.g., headphones, an earpiece, etc.), a medical device (e.g., a biometric sensor, a heart rate monitor, a pedometer, an Electrocardiography (EKG) device, etc.), a user I/O device, a computer, a server, a point-of-sale device, an entertainment device, a set-top box, or any other suitable device. These devices may have different power and data requirements and may result in different power profiles generated for each feature or set of features.

In some aspects a wireless device may comprise an access device (e.g., a Wi-Fi access point) for a communication system. Such an access device may provide, for example, connectivity to another network (e.g., a wide area network such as the Internet or a cellular network) via a wired or wireless communication link. Accordingly, the access device may enable another device (e.g., a Wi-Fi station) to access the other network or some other functionality. In addition, it should be appreciated that one or both of the devices may be portable or, in some cases, relatively non-portable.

Those of skill in the art would understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Those of skill would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The various illustrative logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

In one or more exemplary embodiments, the functions described may be implemented in hardware, software, firmware, or any combination thereof. If implemented in software as a computer program product, the functions may be stored on or transmitted over as one or more instructions or code on a non-transitory computer-readable medium. Computer-readable media can include both computer storage media and communication media including any medium that facilitates transfer of a computer program from one place to another. A storage media may be any available media that can be accessed by a computer. By way of example, and not limitation, such non-transitory computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Also, any connection is properly termed a computer-readable medium. For example, if the software is transmitted from a web site, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and Blu-ray disc where disks usually reproduce data magnetically, while discs reproduce data optically with lasers. Combinations of the above should also be included within the scope of non-transitory computer-readable media.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A method of classifying a motion state of a mobile device comprising:
collecting accelerometer data representing acceleration components along orthogonal x, y, and z axes of the mobile device;
determining a presence or absence of a half-step frequency relationship between the accelerometer data; and
determining the motion state of the device based at least in part on the presence or absence of the half-step frequency relationship.

2. The method of claim 1, wherein the determining of the motion state comprises determining a walk/run state based at least in part on the presence of the half-step frequency relationship.

3. The method of claim 2, further comprising determining an additional activity the user is performing while walking/running.

4. The method of claim 1, further comprising determining whether the user is walking or running based at least in part on an amplitude in the accelerometer data.

5. The method of claim 1, further comprising transforming the accelerometer data from a time domain into a frequency domain, wherein the determining of the presence or absence of the half-step frequency relationship is performed in the frequency domain, and wherein accelerometer data are collected over a time window in the time domain.

6. The method of claim 5, wherein the transforming of the accelerometer data from the time domain into the frequency domain is performed using a Fast Fourier Transform (FFT).

7. The method of claim 5, wherein the time window is at least three seconds in duration.

8. The method of claim 1, wherein the determining of the presence or absence of the half-step frequency relationship occurs in a time domain.

9. An apparatus for classifying a motion state of a mobile device comprising:
a memory; and
a processor configured to:
collect accelerometer data representing acceleration components along orthogonal x, y, and z axes of the mobile device,
determine a presence or absence of a half-step frequency relationship between the accelerometer data, and
determine the motion state of the device based at least in part on the presence or absence of the half-step frequency relationship.

10. The apparatus of claim 9, wherein the determining of the motion state comprises determining a walk/run state based at least in part on the presence of the half-step frequency relationship.

11. The apparatus of claim 10, wherein the processor is further configured to determine an additional activity the user is performing while walking/running.

12. The apparatus of claim 9, wherein the processor is further configured to determine whether the user is walking or running based at least in part on an amplitude in the accelerometer data.

13. The apparatus of claim 9, wherein the processor is further configured to:
transform the accelerometer data from a time domain into a frequency domain, wherein the determining of the presence or absence of the half-step frequency relationship is performed in the frequency domain, and
wherein accelerometer data are collected over a time window in the time domain.

14. The apparatus of claim 13, wherein the transforming of the accelerometer data from the time domain into the frequency domain is performed using a Fast Fourier Transform (PIT).

15. The apparatus of claim 13, wherein the time window is at least three seconds in duration.

16. The apparatus of claim 9, wherein the determining of the presence or absence of the half-step frequency relationship occurs in a time domain.

17. An apparatus for classifying a motion state of a mobile device comprising:
means for collecting accelerometer data representing acceleration components along orthogonal x, y, and z axes of the mobile device;
means for determining a presence or absence of a half-step frequency relationship between the accelerometer data; and
means for determining the motion state of the device based at least in part on the presence or absence of the half-step frequency relationship.

18. The apparatus of claim 17, wherein the means for determining the motion state comprises means for determining a walk/run state based at least in part on the presence of the half-step frequency relationship.

19. The apparatus of claim 18, further comprising means for determining an additional activity the user is performing while walking/running.

20. The apparatus of claim 17, further comprising means for determining whether the user is walking or running based at least in part on an amplitude in the accelerometer data.

21. The apparatus of claim 17, further comprising means for transforming the accelerometer data from a time domain into a frequency domain, wherein the determining of the presence or absence of the half-step frequency relationship is performed in the frequency domain, and
wherein accelerometer data are collected over a time window in the time domain.

22. The apparatus of claim 21, wherein the transforming of the accelerometer data from the time domain into the frequency domain is performed using a Fast Fourier Transform (PIT).

23. The apparatus of claim 21, wherein the time window is at least three seconds in duration.

24. The apparatus of claim 17, wherein the determining of the presence or absence of the half-step frequency relationship occurs in a time domain.

25. A non-transitory computer-readable medium including code which, when executed by a processor, causes the processor to perform a method comprising:
collecting accelerometer data representing acceleration components along orthogonal x, y, and z axes of the mobile device;
determining a presence or absence of a half-step frequency relationship between the accelerometer data; and
determining the motion state of the device based at least in part on the presence or absence of the half-step frequency relationship.

26. The non-transitory computer-readable medium of claim 25, wherein the determining of the motion state comprises determining a walk/run state based at least in part on the presence of the half-step frequency relationship.

27. The non-transitory computer-readable medium of claim 26, further comprising code for determining an additional activity the user is performing while walking/running.

28. The non-transitory computer-readable medium of claim 25, further comprising code for determining whether the user is walking or running based at least in part on an amplitude in the accelerometer data.

29. The non-transitory computer-readable medium of claim 25, further comprising code for transforming the accelerometer data from a time domain into a frequency domain, wherein the determining of the presence or absence of the half-step frequency relationship is performed in the frequency domain, and
    wherein accelerometer data are collected over a time window in the time domain.

30. The non-transitory computer-readable medium of claim 29, wherein the transforming of the accelerometer data from the time domain into the frequency domain is performed using a Fast Fourier Transform (FFT).

31. The non-transitory computer-readable medium of claim 29, wherein the time window is at least three seconds in duration.

32. The non-transitory computer-readable medium of claim 25, wherein the determining of the presence or absence of the half-step frequency relationship occurs in a time domain.

* * * * *